United States Patent
Muhr et al.

(10) Patent No.: US 6,172,257 B1
(45) Date of Patent: Jan. 9, 2001

(54) PROCESS FOR PREPARING POTASSIUM MONOETHYL MALONATE

(75) Inventors: Juergen Muhr, Alfter; Marcel Feld, Cologne, both of (DE)

(73) Assignee: Creanova Spezialchemie GmbH, Marl (DE)

(*) Notice: Under 35 U.S.C. 154(b), the term of this patent shall be extended for 0 days.

(21) Appl. No.: 09/294,011

(22) Filed: Apr. 19, 1999

(30) Foreign Application Priority Data

Apr. 17, 1998 (DE) .............................................. 198 17 101

(51) Int. Cl.[7] .......................... C07C 69/38; C07C 67/30
(52) U.S. Cl. .............................................. 560/190; 560/191
(58) Field of Search ..................... 560/190, 191

(56) References Cited

U.S. PATENT DOCUMENTS 3,855,229 * 12/1974 Razdan et al. ................... 260/293.58
5,750,550 * 5/1998 Eissenstat et al. .................... 514/373

FOREIGN PATENT DOCUMENTS 0 720 981 A1 7/1996 (EP) .

OTHER PUBLICATIONS

Breslow, D. S., et al. "A new synthesis of beta–keto esters of the type RCOCH2COOEt" J. Am. Chem. Soc. vol. 66 No. 7 pp. 1286–1288, Aug. 1944.*

Strube, R. E. "Ethyl t–butyl malonate" Org. Syn coll vol. 4, pp. 417–419, Jul. 1963.*

Box et al, "The Synthesis of Beta–Lactones and Beta–Lactams from Malonates and Malonamides", Heterocycles, vol. 32 No. 2., 1991, 245–251.

van't Hoff (Ber. Dtsch. Chem. Ges. 7, 1572).

* cited by examiner

Primary Examiner—Howard C. Lee
Assistant Examiner—Leigh C. Maier
(74) Attorney, Agent, or Firm—Oblon, Spivak, McClelland, Maier & Neustadt, P.C.

(57) ABSTRACT

A process for preparing potassium monoethyl malonate by selective saponification of malonic acid diethyl ester with potassium hydroxide, in which the potassium hydroxide is added to the malonic acid diethyl ester, malonic acid diethyl ester and potassium hydroxide are used in a molar ratio of at least 1.5 and the potassium hydroxide is effectively distributed into the malonic acid diethyl ester.

11 Claims, No Drawings

PROCESS FOR PREPARING POTASSIUM MONOETHYL MALONATE

BACKGROUND OF THE INVENTION

1. Field of the Invention

The invention relates to a process for preparing potassium monoethyl malonate (or the potassium salt of malonic acid monoethyl ester; designated KEM hereafter) by selective saponification of diethyl malonate (or malonic acid diethyl ester; designated DEM hereafter) with potassium hydroxide, the target product being obtained in high purity.

2. Discussion of the Background

KEM is used as a precursor for the syntheses of pharmaceuticals having a quinolone structure. The use for syntheses in the pharmaceutical area, however, requires high product purity. In particular, a significant content of dipotassium malonate (designated DKM hereafter) is undesired.

A synthesis of potassium monoethyl malonate which was described as early as in the last century by van't Hoff (*Ber. Dtsch. Chem. Ges.* 7, 1572) and which is still currently practiced starts from DEM which is selectively saponified with potassium hydroxide. According to EP 0 720 981 A1, this is performed using equimolar amounts of starting material in an alcoholic medium. However, the sought-after selective saponification is achieved only to an inadequate extent, so that only a target product considerably contaminated with dipotassium malonate (DKM) is obtained. The content of DKM is customarily in the order of magnitude of several % by weight. Removal of the dipotassium malonate from the potassium monoethyl malonate which is necessary for use of the latter as a pharmaceutical precursor is difficult and includes extensive purification operations. A further disadvantage of the known process is the relatively high dilution at which the process must be carried out. The alcohol is used at 19 to 28 times the amount by weight of potassium hydroxide. This large amount of alcohol has an adverse effect on the space-time yield and increases the expense for recovery of the solvent. In the case of the processes mentioned, the amount of alcohol is further increased by the DEM likewise being used in alcoholic solution.

Box et al., *Heterocycles*, Vol. 32, No. 2, 1991, 245 ff., describe a synthesis of β-lactones and β-lactams, in which KEM is as intermediate. The two starting materials are, as in the process described in EP 0 720 981 A1 discussed above, used in equimolar amounts, that is to say each at 100 mmol. The molar ratios of DEM to KOH were calculated incorrectly, however, since 20.225 g of DEM is 126 mmol and is equivalent to 1.26 times the molar amount, based on KOH. If it is further assumed that the potassium hydroxide used had, as is commercially usual, a KOH content of approximately 90% by weight (remainder water), 20.225 g of DEM are actually equivalent to 1.38 times the molar amount, based on KOH (calculated as 100%). Working using molar ratios of 1.26:1 and 1.38:1 showed that although pure KEM containing less than 0.5% by weight of DKM was obtainable by this process, the precipitated KEM was really difficult to filter. In the case of laboratory batches, the filtration time was more than two hours. Such times are prohibitive for production on an industrial scale. In addition, according to Box et al., similar to the process of EP 0720 981 A1 cited above, considerable amounts of alcohol are required. Finally, the yields of KEM are not satisfactory either.

SUMMARY OF THE INVENTION

One of the objects of the present invention is to provide a process for preparing potassium monoethyl malonate which avoids the above disadvantages, i.e., gives high yields of a pure low-DKM and readily filterable KEM without the use of large amounts of alcohol.

This object, and others, is achieved by a process for preparing potassium monoethyl malonate by selective saponification of malonic acid diethyl ester with potassium hydroxide, in which the potassium hydroxide is added to the malonic acid diethyl ester, malonic acid diethyl ester and potassium hydroxide are used in a molar ratio of at least 1.5 and the potassium hydroxide is effectively distributed in the malonic acid diethyl ester.

A more complete appreciation of the invention and many of the attendant advantages thereof will be readily obtained as the same becomes better understood by reference to the following detailed description.

DETAILED DESCRIPTION OF THE INVENTION

The process according to the present invention provides potassium monoethyl malonate that may have a DKM content of <1% by weight (such as at most 0.1, 0.2, 0.3, 0.5, 0.8 or 1% by weight), as required for pharmaceutical syntheses, shows acceptable filtration times and requires a comparatively low energy consumption for recovery of the alcohol and of the excess malonic acid diethyl ester. The high purity of the KEM was surprising, since the measures according to the invention do not show a comparable effect in the case of the homologous malonic acid dimethyl ester (or dimethyl malonate; DMM). The Comparison Examples 2 and 3 show that DMM, even without the molar ratio of KOH to DEM according to the invention and even without effective distribution of the potassium hydroxide, gives a potassium monomethyl malonate (KMM) having low contents of DKM. In addition, it was surprising, and critical for production on an industrial scale, that the KEM according to the invention is very readily filterable, as can be seen from Comparison Example 6. This effect is difficult to explain, even with hindsight. Finally, it is surprising, that sodium monoethyl malonate (NaEM), analogous to the KEM, under the conditions according to the invention gives an NaEM having a high content of disodium malonate (DNaM), furthermore in poor yield, as Comparison Example 4 shows. In addition, there is the fact that the NaEM reaction mixture is considerably more difficult to filter than the corresponding KEM mixture in the present process according to the invention. Filtration of the first lasts approximately ten times as long, with correspondingly poorer space-time yield An important feature of the process according to the invention is that the potassium hydroxide is added to the malonic acid diethyl ester which is therefore present in excess over the entire course of the reaction. The potassium hydroxide is advantageously used in the form of a solution in particular an alcoholic solution. In order to avoid transesterifications, preferably ethanol is used as the alcoholic solvent. For this purpose, the approximately 96 percent by weight ethanol can be used, as is produced as an azeotrope in the distillation of aqueous alcoholic mixtures. Alternatively, ethanol having other, similarly low, water contents can be used, or preferably the so-called absolute anhydrous alcohol can be used. The solution can contain other inert low-boiling solvents, such as aliphatic, cycloaliphatic or aromatic hydrocarbons, without particular advantage being associated therewith. In the solution, the alcohol and, if appropriate, other solvents, are generally present at 3 to 10 times, advantageously 4 to 8 times, the amount by weight, based on potassium hydroxide. These ranges include all specific values and subranges therebetween, such as 3.5, 4.5, 5, 6, 7 and 9 times the amount of potassium hydroxide. The process according to the invention therefore succeeds with less alcohol or solvent than the known processes described above.

Another important feature of the present process is the molar excess in which the malonic acid diethyl ester is used, more precisely advantageously without added solvent or diluent. At a molar ratio of 1.5 to 12 mol, preferably 2 to 8 mol, and in particular 3 to 5 mol, malonic acid diethyl ester per mole of potassium hydroxide, on the one hand the high product purity which is characteristic of the process according to the invention is achieved, and on the other hand the reaction mixture, despite the target product precipitating in crystalline form, is ensured to remain handleable as a suspension. These ranges for the molar ratio of malonic acid diethyl ester to potassium hydroxide including 2.5, 4, 4.5, 5.5, 6, 7, 9, 10 and 11 mol. The excess can be less, within the specified limits, if the amount of the alcohol or further solvent used for the potassium hydroxide solution is within the upper range within the limits specified therefor. The excess malonic acid diethyl ester can be virtually completely recovered by distillation.

Another important aspect of the invention is the effective distribution (or thorough mixing) of the added potassium hydroxide in the excess malonic acid diethyl ester by action of shear forces on the mixture. This can be achieved, for example, by particularly effective stirring and/or by forced circulation of the reaction mixture, if appropriate, through tubes having mixing-promoting internals and/or through mixing nozzles. The feature "effective distribution" is, as will be well-recognized, not amenable to quantitative description. The optimum distribution (or effective mixing) can be determined without difficulty by preliminary experiments. It is achieved when an increase in energy input under otherwise identical conditions does not give an improvement in yield and/or product quality.

The process of the invention is advantageously carried out at temperatures of <80° C. preferably <60° C., and in particular 0° C. to about 30° C. These temperature ranges include all specific values and subranges therebetween, including 5, 10, 15, 25, 35, 40, 45, 50, 65, 70 and 75° C. Under these conditions, the partial saponification of the malonic acid diethyl ester proceeds rapidly and selectively. The reaction is virtually complete when all of the potassium hydroxide has been fed; a longer postreaction time is not necessary. After completion of the reaction, the temperature can be increased, if appropriate with low-boiling fractions, such as ethanol or other low-boiling solvents, being distilled off.

The process according to the invention can be carried out batchwise, for example, by introducing the malonic acid diethyl ester at room temperature into a stirred reactor and allowing a very low-water or anhydrous solution of potassium hydroxide in ethanol to flow in a little at a time with intensive mixing in the course of 30 minutes to 4 hours. The mixing intensity here determines the rate at which the potassium hydroxide solution is added. The malonic acid diethyl ester can be used undiluted or can contain solvent fractions, for example if recovered excess malonic acid diethyl ester is used or used in conjunction. Depending on the amount of the starting materials used, the temperature remains in the specified range without further measures, or indirect cooling is used to ensure that the temperature remains in this range.

In a continuous embodiment of the process, the potassium hydroxide solution is added to the excess malonic acid diethyl ester and the mixture is conducted via a distribution nozzle to a mixing section in which partial saponification proceeds in the course of seconds up to a few minutes.

The target product potassium monoethyl malonate is produced in solid form and, when the reaction is complete, if appropriate continuously also, can be separated off by conventional solid/liquid, separation, for example using a vacuum filter, filter press or centrifuge. By extraction with a low-boiling solvent, expediently an alcohol, adhering excess malonic acid diethyl ester is removed. It is a further advantage of the process according to the invention that the potassium monoethyl malonate is produced in a readily filterable and easily extractable form, which likewise contributes to the high product purity and the comparatively low solvent requirement. The mother liquor obtained as filtrate and the washing liquid can, after removal of the alcohol formed in the partial saponification or introduced together with the potassium hydroxide, as well as, if appropriate, solvents introduced in addition into the reaction and, after supplementation of the malonic acid diethyl ester consumed, be recycled to the process as starting material and reaction medium, i.e., used for a new batch or recycled to the continuous process. The alcohol and the solvent can be removed under gentle conditions, i.e., at reduced pressure and/or with conjoint use of an azeotrope-forming inert entrainer. This counteracts the formation of unwanted byproducts. Examples of inert entrainers which facilitate distilling off the alcohol which may be mentioned are, in particular, aliphatic and/or aromatic hydrocarbons which can be added when the reaction is complete or even during or before the reaction.

The yield of the isolated KEM is preferably as high as possible. The yield may be at least 50%, preferably at least 75%, more preferably at least 90%, even more preferably at least 95%, and most preferably even higher, such as 96%, 97%, 98%, 99% or 100%.

Having generally described this invention, a further understanding can be obtained by reference to certain specific examples which are provided herein for purposes of illustration only and are not intended to be limiting unless otherwise specified.

EXAMPLES

Example 1

Preparation of KEM

A solution of 111.1 g of KOH (91% pure by weight—1.8 mol) in 500 g of 98% pure ethanol is added to 900 g of DEM (5.6 mol) at 15–20° C. in the course of about 2 h with intensive mixing. The mixing is performed by a KPG agitator which is operated at 300 rpm. The resulting suspension is filtered off. Filtration by means of a suction filter and water-jet vacuum takes approximately 3 min. The filtration residue is washed with ethanol and dried in vacuo. 261.9 g of KEM are obtained, equivalent to 85.5% of theory, based on KOH. The content of DKM is 0.3% by weight. It was determined here, and in the examples below, by ion chromatography.

The low-boilers are recovered from the filtrate and the washing liquid by distillation. The bottom-phase residue contains the excess DEM and KEM remaining dissolved or redissolved during washing. DEM consumed by reaction is replaced and, in a new batch, KOH solution prepared from the recovered low-boilers is added. In this manner, after a plurality of recycling steps, KEM is obtained having a mean yield of about 95% of theory and a mean DKM content of <0.6% by weight.

Comparison Example 1

Preparation of Potassium Monoethyl Malonate

The procedure of Example 1 is followed, but only 320.4 g of DEM (2.1 mol) are introduced and the KPG agitator is operated at 50 rpm. 252.5 g of KEM are obtained, equivalent to 82.6% of theory, having a DKM content of >5% by weight.

Example 1 and Comparison Example 1 show that the combination of excess DEM with good mixing improves the yield and the product quality.

Comparison Example 2

Preparation of Potassium Monomethyl Malonate (KMM)

111.6 g of KOH (1.8 mol) are dissolved in 500 g of methanol, and the solution is added to 264.2 g of dimethyl malonate (2 mol) in the course of 2 h at room temperature. The KPG agitator is operated during this at 50 rpm. This mixes the reaction suspension inadequately, broad edge zones remain virtually unmixed. The reaction suspension is then filtered and the filtration residue is washed with methanol and dried in vacuo. 214.2 g of KMM are is obtained, equivalent to a yield of 76% of theory having a DKM content of <0.2% by weight.

Comparison Example 3

Preparation of Potassium Monomethyl Malonate

The procedure of Comparison Example 1 is followed, but the KPG stirrer is operated at 200 rpm, and 217.8 g of KMM are obtained, equivalent to 77.5% of theory, having a DKM content of <0.2% by weight.

Comparison Examples 2 and 3 show that, in KMM preparation, the type of mixing has no effect on yield and product quality.

Comparison Example 4

Preparation of Sodium Monoethyl Malonate (NaME)

The procedure of Example 1 is followed, but instead of potassium hydroxide solution, 429 g of 12.6 percent strength by weight sodium hydroxide solution (1.4 mol NaOH) is used. 39.0 g of NaME are obtained, equivalent to 15.2% of theory, having a disodium malonate (DNaM) content of 18.6%.

The comparison example shows that an excess of DEM and vigorous mixing in the case of NaME do not lead to the yields and product quality which are achieved with KEM.

Comparison Example 5

Preparation of Potassium Monoethyl Malonate (KMM)

28.2 g of KOH (91% purity by weight; 0.46 mol) are dissolved in 500 ml of 98% strength ethanol. The solution is added dropwise within the course of 1 h to a solution of 100.9 g of DEM (0.63 mol) in 500 ml of 98% pure ethanol, which is stirred by a KPG stirrer (250 rpm), the temperature being kept to 0° C. The reaction mixture is allowed to heat to room temperature and it is agitated for a further hour, the precipitated crystals are removed by vacuum filtration (water-jet vacuum) and washed with 98% pure alcohol. The filtration required 2.3 h. 53.3 g of KEM were obtained, equivalent to 68.8% of theory, having a DKM content of 0.1% by weight.

The comparison example shows that, although the procedure according to Box et al. (loc.cit) gives a highly pure KEM, it is in unsatisfactory yields, and in addition with the use of large amounts of ethanol and with long filtration times.

Obviously, numerous modifications and variations of the present invention are possible in light of the above teachings. It is therefore to be understood that within the scope of the appended claims, the invention may be practiced otherwise than as specifically described herein.

This Application is based on German Patent Application 198 17 101.3, filed on Apr. 17, 1997, and incorporated herein by reference in its entirety.

What is claimed is:

1. A process for preparing potassium monoethyl malonate, comprising:
   adding potassium hydroxide to malonic acid diethyl ester at a temperature of 0 to 30° C. to produce potassium monoethyl malonate,
   wherein the molar ratio of the malonic acid diethyl ester to the potassium hydroxide is at least 1.5;
   wherein the yield of the isolated potassium monoethyl malonate is at least 90%; and
   wherein the purity of the isolated potassium monoethyl malonate is at least 99.4%.

2. The process of claim 1, wherein the potassium hydroxide is added to the malonic acid diethyl ester in the form of an ethanolic solution.

3. The process of claim 1, wherein the ethanolic solution further comprises one or more additional inert low-boiling solvents.

4. The process of claim 1, wherein the molar ratio of the malonic acid diethyl ester to the potassium hydroxide is 1.5 to 12.

5. The process of claim 1, wherein the molar ratio of the malonic acid diethyl ester to the potassium hydroxide is 2 to 8.

6. The process of claim 1, wherein the molar ratio of the malonic acid diethyl ester to the potassium hydroxide is 3 to 5.

7. The process of claim 1, wherein the mother liquor obtained after removal of solid potassium monoethyl malonate and the washing liquid, after separating off the alcohol formed and inert low-boiling solvents additionally introduced into the reaction, and after supplementation of the malonic acid diethyl ester consumed, are recycled to the process as starting material and reaction medium.

8. The process of claim 1, wherein the potassium hydroxide is used in the form of an alcoholic solution and the malonic acid diethyl ester is used without added solvent or diluent, and the alcohol is used in 3 to 10 times the amount by weight, based on potassium hydroxide.

9. The process of claim 1, further comprising isolating the potassium monoethyl malonate.

10. The process of claim 9, wherein the isolated potassium monoethyl malonate contains at most 0.6% by weight of dipotassium malonate.

11. The process of claim 9, wherein the yield of the isolated potassium monoethyl malonate is at least 95%.

* * * * *

UNITED STATES PATENT AND TRADEMARK OFFICE
CERTIFICATE OF CORRECTION

PATENT NO. : 6,172,257

DATED : Jan. 9, 2001

INVENTOR(S): Juergen MUHR, et al.

It is certified that an error appears in the above-identified patent and that said Letters Patent is hereby corrected as shown below:

On the Title page, the CPA information has been omitted. It should read as follows:

-- (45)  Date of Patent: * Jan. 9, 2001 --

-- (*) Notice: This Patent issued on a continued prosecution application filed under 37 CFR 1.53(d), and is subject to the twenty year patent term provisions of 35 U.S.C. 154(a)(2).

Signed and Sealed this

Eighth Day of May, 2001

*Attest:*

NICHOLAS P. GODICI

*Attesting Officer*  Acting Director of the United States Patent and Trademark Office